United States Patent [19]
O'Hare et al.

[11] Patent Number: 6,017,735
[45] Date of Patent: Jan. 25, 2000

[54] MATERIALS AND METHODS FOR INTRACELLULAR TRANSPORT AND THEIR USES

[75] Inventors: Peter Francis Joseph O'Hare; Gillian Daphne Elliott, both of Oxted, United Kingdom

[73] Assignee: Marie Curie Cancer Care, London, United Kingdom

[21] Appl. No.: 09/012,126

[22] Filed: Jan. 22, 1998

[30] Foreign Application Priority Data

Jan. 23, 1997 [GB] United Kingdom .................... 9701363
Aug. 1, 1997 [GB] United Kingdom .................... 9716398

[51] Int. Cl.$^7$ ........................... C12N 15/09; C12N 15/62; C12N 5/10; C07K 19/00
[52] U.S. Cl. .................... 435/69.7; 435/69.3; 435/320.1; 435/252.3; 435/325; 435/317.1; 536/23.4; 536/23.5; 530/350
[58] Field of Search ..................................... 530/350, 402; 435/69.3, 69.7, 320.1, 252.3, 325, 317.1; 536/23.4, 23.5

[56] References Cited

FOREIGN PATENT DOCUMENTS 0 475 623 A1  3/1992  European Pat. Off.
WO 97/04092  2/1997  WIPO.

OTHER PUBLICATIONS

Mercer et al., Wide type human p53 is antiproliferative in SV40–transformed hamster cells, Oncogene, vol. 5, pp. 973–980 (1990).

Shaw et al., Induction of apoptosis by wild–type p53 in human colon tumor–derived cell line, Proc. Natl. Acad. Sci., vol. 89, pp. 4495–4499 (1992).

Baker et al., Suppression of Human Colorectal Carcinoma Cell Growth by Wild–Type p53, Science, vol. 249, pp. 912–915 (1990).

Nicholson et al., "Localization of the herpes simplex virus type 1 major capside protein VP5 to cell nucleus requires the abundant scaffolding protein VP22a, " Journal of General Virology, vol. 75, No. 5, pp. 1091–1099 (1994).

Elliott et al., "VP16 interacts via its activation domain with VP22,a tegument protein of herpes simplex virus, and is relocated to a novel macromolecular assembly in coexperessing cells," Journal of Virology, vol. 69(12), pp. 7932–7941 (1995).

Elliott & O'Hare, "Intercellular Trafficking and Protein Delivery by a Herpesvirus Structural Protein," Cell, vol. 88, pp. 223–233 (1997).

Leslie, J. et al. Virology 220: 60–68, 1996.

*Primary Examiner*—Mary E. Mosher
*Attorney, Agent, or Firm*—Klarquist Sparkman Campbell Leigh & Whinston, LLP

[57] ABSTRACT

Coupled polypeptides and fusion polypeptides for intracellular transport, and their preparation and use, include (i) an aminoacid sequence with the transport function of herpesviral VP22 protein (or a homologue, e.g. from VZV, BHV or MDV) and (ii) another protein sequence selected from (a) proteins for cell cycle control; (b) suicide proteins; (c) antigenic sequences or antigenic proteins from microbial and viral antigens and tumour antigens; (d) immunomodulating proteins; and (e) therapeutic proteins. The coupled proteins can be used for intracellular delivery of protein sequences (ii), to exert the corresponding effector function in the target cell, and the fusion polypeptides can be expressed from corresponding polynucleotides. vectors and host cells.

19 Claims, 6 Drawing Sheets

p4953ep+10 anti-VP22

FIG 1(e)

p4953ep+10 anti-p53

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 1

Arg Ser Ala Ser Arg
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 2

Arg Ser Ala Ala Ser Arg
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 3

Arg Thr Ala Ser Arg
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 4

Arg Thr Ala Ala Ser Arg
 1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 5

Arg Ser Arg Ala Arg
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 6

Arg Ser Arg Ala Ala Arg
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 7

Arg Thr Arg Ala Arg
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 8

Arg Thr Arg Ala Ala Arg
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 9

Ala Thr Ala Thr Arg
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 10

Ala Thr Ala Ala Thr Arg
 1               5

<210> SEQ ID NO 11
<211> LENGTH: 24
```

```
<212> TYPE: PRT
<213> ORGANISM: Artificial Sequence
<220> FEATURE:
<223> OTHER INFORMATION: Description of Artificial Sequence: linker
      sequence

<400> SEQUENCE: 11

Arg Val Cys Ser Asn Pro Pro Cys Glu Thr His Glu Thr Gly Thr Thr
 1               5                  10                  15
Asn Thr Ala Thr Ala Thr Ser Asn
             20
```

MATERIALS AND METHODS FOR INTRACELLULAR TRANSPORT AND THEIR USES

FIELD OF THE INVENTION

The present invention concerns improvements, modifications and developments in relation to transport proteins, intracellular transport and their applications. In particular embodiments, the invention relates to fusion proteins comprising transport proteins comprising sequences from herpesviral VP22 or from homologues or fragments thereof together with sequences from other proteins; and to methods for their preparation and use. In particular embodiments, the invention relates to fusion proteins for cell cycle control, and to materials and methods for their preparation and their use. In particular examples the invention relates to fusion proteins having both mammalian p53 functionality and herpesviral VP22 functionality. Other aspects of the invention will be apparent from the description and claims.

BACKGROUND OF THE INVENTION, AND PRIOR ART

Figure 1A:
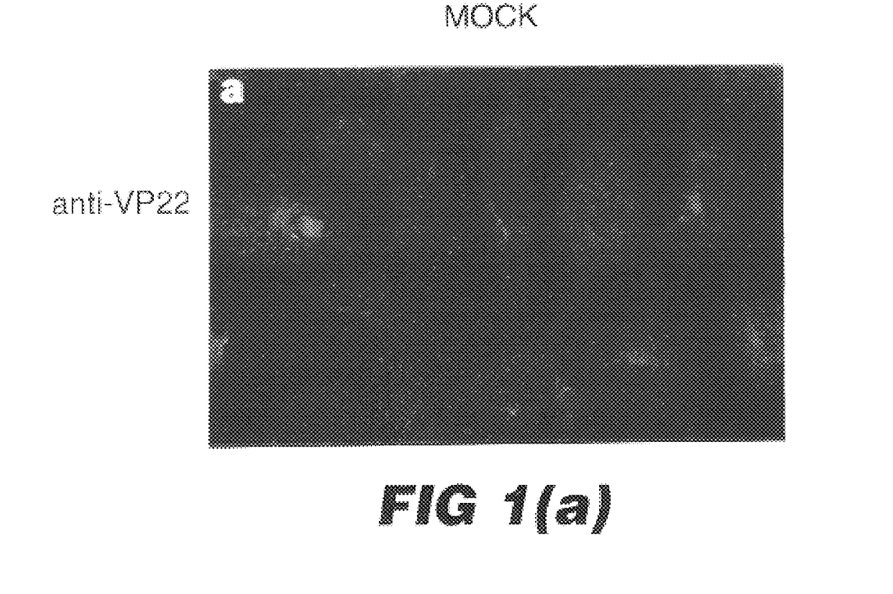
Figure 1B:
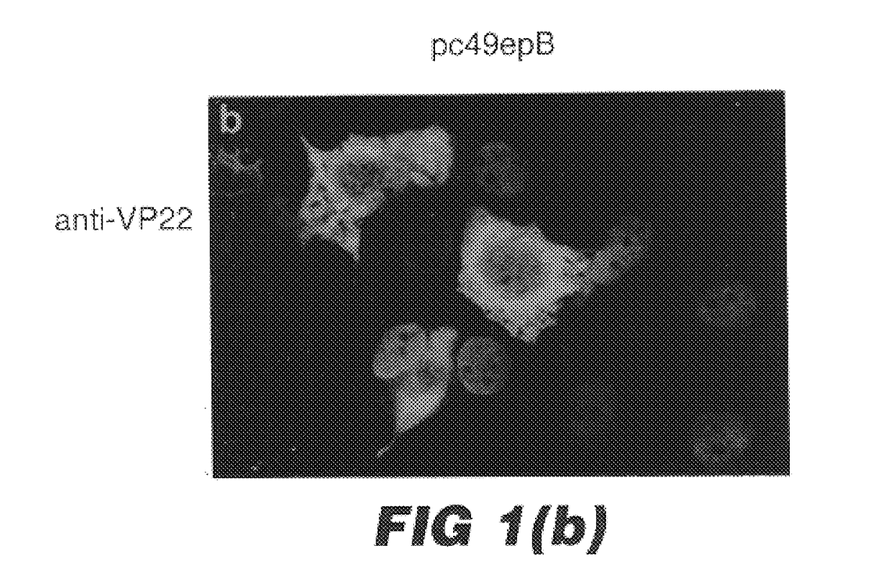

Relevant to the present application is the inventors' own earlier international patent application WO 97/05265 (O'Hare and Elliott) (published after the priority date claimed for this application), which relates to VP22 protein and its properties and uses. Similarly the inventors' paper (Elliott and O'Hare (1997), in Cell, vol 88 pp 223–233 (1997), relates to intercellular trafficking and protein delivery by a herpesvirus structural protein. Both these documents are hereby incorporated in their entirety by reference and made an integral part of this disclosure, The inventors have shown that the HSV-1 virion protein VP22 possesses an unusual intercellular trafficking mechanism, an effect particularly described in specification WO 97/05265. VP22 is a 38 kDa protein which in primary-expressing transfected mammalian cells is located predominantly in the cytoplasm where it associates with cellular microtubules (see accompanying drawing, FIG. 1b). However a remarkable property of VP22 is its ability to spread throughout a monolayer of non-expressing cells. VP22 is transported from the cytoplasm of an expressing cell into neighbouring cells where it accumulates in the nucleus (FIG. 1b). The mechanism of this transport is still incompletely understood, but has been shown to be via a golgi-independent pathway and may utilise the actin cytoskeleton. HIV-1 Tat (Ensoli et al., 1993, Fawell et. al., 1994) and a small number of other non-viral proteins (Jackson et al., 1992) have been attributed with intercellular trafficking properties, but none appears to demonstrate this phenomenon as strikingly as VP22. A further important property of VP22 is that when applied exogenously to the medium of an untransfected cell monolayer, it can be taken up by these untransfected cells where it accumulates in the cell nucleus.

The prior art generally includes a variety of antigens, immunomodulating proteins, proteins that are conditionally cytotoxic or lethal upon administration (to a cell containing them) of a corresponding drug or activator compound, proteins for cell cycle control, and other therapeutic and diagnostic proteins, especially in the forms of protein and polynucleotide sequences enabling genetic manipulation by standard techniques. References to some examples of these materials are given below.

Figure 1C:
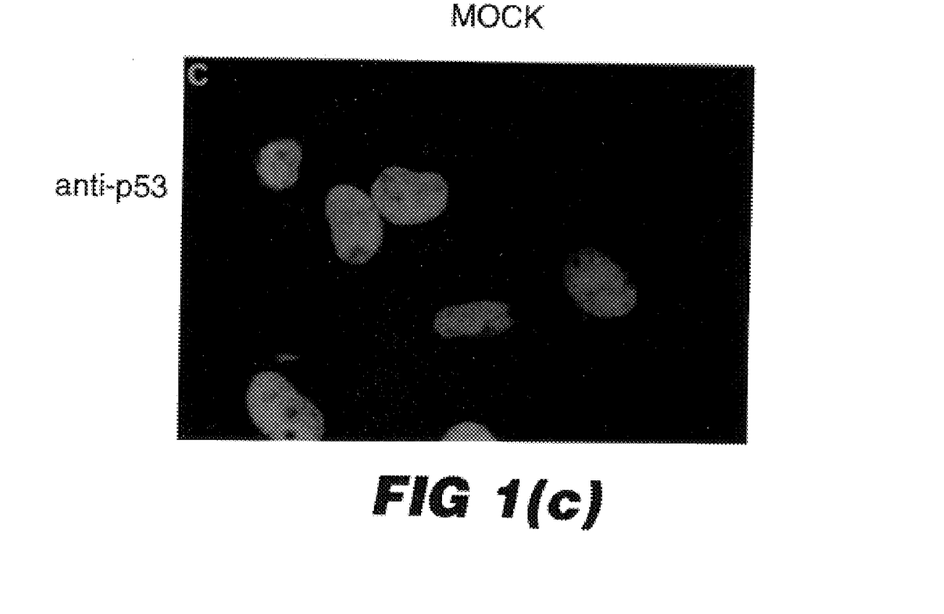
Figure 1D:
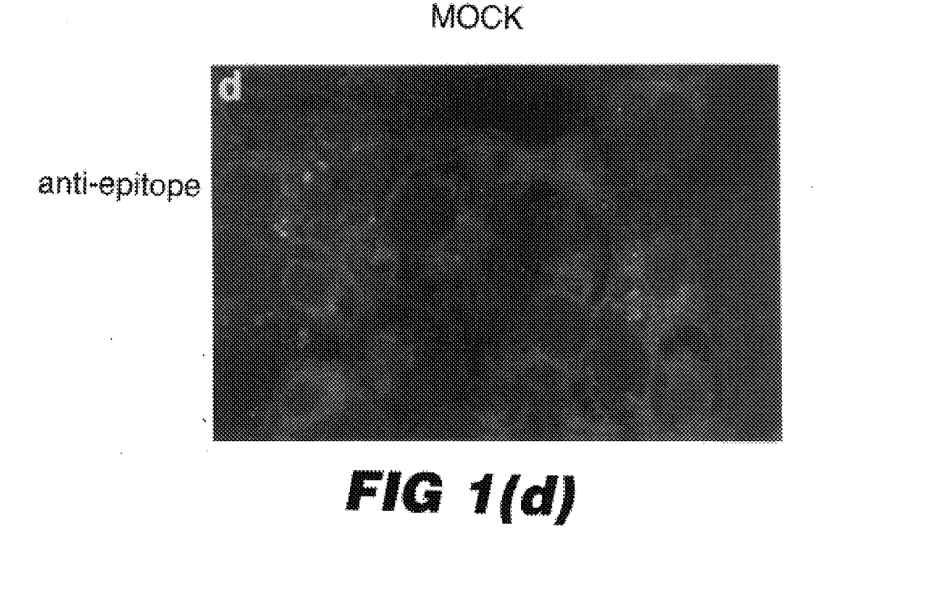

For example, among cell cycle control proteins, protein p53 is known as a tumour suppressor. p53 is a 53 kDa nuclear phosphoproprotein (FIG. 1c). Wild-type and mutant p53 proteins have been expressed by means of recombinant vaccinia viruses, (Ronen et al., Nucleic Acids Research, 20:3435–3441, 1992). p53 functions to regulate cell cycle progression and under conditions of DNA damage through a complex signal transduction mechanism can induce cell cycle arrest or apoptosis (Levine 1997). Failure to synthesize p53, or more commonly synthesis of a mutated form of the protein can result in uncontrolled cell proliferation and tumour formation. It has been shown by several groups that exogenous addition of functional wild type p53 can promote cell cycle arrest and/or apoptosis resulting in tumour regression with examples including cervical carcinomas (Hamada et al., 1996) and breast cancer xenografts (Nielsen et al., 1997). A number of p53 delivery systems have been utilised in vivo and in vitro such as intravenous injection of a p53:liposome complex (Kumar et al., 1997), direct transfection (Zheng et al., 1996) and adenoviral mediated transfer (Hamada et al., 1996, Sandig et al., 1997) but delivery of functional protein into a sufficiently high percentage of surviving cells remains a difficulty.

Also known from U.S. Pat. No. 5,484,710 (La Jolla: J. C. Reed et al) are regulatory elements linked to genes involved in cell death, as regulated by p53 tumour suppressor protein, and further proteins and their analogues for cell cycle control.

It remains desirable to provide particular further cell-delivery constructs for useful proteins.

SUMMARY AND DESCRIPTION OF THE INVENTION

According to an aspect of the present invention, there are provided coupled proteins comprising transport protein sequences comprising sequences from herpesviral VP22 or from homologues or fragments thereof, together with sequences from other proteins selected from: (a) proteins for cell cycle control; (b) proteins that are conditionally cytotoxic or lethal upon administration (to a cell containing them) of a corresponding drug, pro-drug or activator compound (otherwise described herein as suicide proteins); (c) antigenic sequences or antigenic proteins (e.g. of greater than 12 aminoacid residues in length) from microbial and viral antigens and tumour antigens; (d) immunomodulating proteins; and (e) therapeutic proteins. Examples of these kinds of proteins mentioned below. Thus, coupling or fusion to an aminoacid sequence with the transport function of VP22 protein can provide a useful cell delivery construct for proteins of the kinds mentioned. (Where the context admits, 'coupling products' and similar expressions include reference to fusion proteins.)

Preferably the coupled proteins are fusion proteins, which can conveniently be expressed in known suitable host cells. Corresponding polynucleotide sequences can be prepared and manipulated using elements of per-se known and standard recombinant DNA technique and readily available adaptations thereof. However, chemically-coupled products can for certain applications be used if desired, and can be prepared from the individual protein components according to any of a variety of per-se known chemical coupling techniques.

VP22 or a functional sub-sequence thereof, optionally with an additional polypeptide tail for coupling, can be linked to other proteins or nucleic acid by chemical coupling in any known suitable standard manner.

Also provided by the invention are polynucleotides encoding the fusion proteins as described herein, including sequences corresponding to VP22 and another protein of one of the kinds mentioned above, and expression cassettes, plasmids, vectors and recombinant cells comprising the polynucleotides. These can be formed and used in ways analogous to or readily adaptable from standard recombinant DNA technique. Thus, corresponding polynucleotides can encode a fusion polypeptide that comprises a sequence with the transport function of herpesviral VP22 protein and a sequence with one of the functions specified herein. The polynucleotide can be comprised in an open reading frame operably linked to a suitable promoter sequence, and can according to examples of the invention form part of an expression vector, e.g. comprising the polynucleotide carried in a plasmid. The expression vector can be for example a recombinant virus vector or a non-viral transfection vector. The vectors can for example be analogues or examples of those vectors mentioned or described in WO97/05265, or of those mentioned or described in WO 92/05263, WO 94121807, or WO 96/26267. For nucleotide sequence that are capable of being transcribed and translated to produce a functional polypeptide, degeneracy of the genetic code results in a number of nucleotide sequences that encode the same polypeptide. The invention includes all such sequences.

Thus products described herein can be used according to the invention as transportable proteins capable of being taken up by a target population of cells, e.g. so that an effector function corresponding to the polypeptide sequence coupled to the VP22, from among the kinds mentioned above, can take place within the target cells that have taken up the product. Thus, for example, the target cells may present desired tumour antigen epitopes in a case where the polypeptide sequence is from a chosen tumour antigen, or become subject to cell cycle control effects where the the polypeptide sequence is from a cell cycle control protein, or become in some degree susceptible to cell killing or injury after additional treatment with a prodrug where the polypeptide sequence is from a corresponding 'suicide protein'. In use, many of the products described herein can be expressed as fusion proteins in a first part of the target population of cells, exported therefrom, and taken up by a second part of the target population of cells not directly producing the protein. Also within the invention are mammalian and microbial host cells comprising such vectors or other polynucleotides encoding the fusion proteins, and their production and use.

A fusion polypeptide as described herein can be transported to a target population of cells, by introducing a polynucleotide or other vector encoding the fusion polypeptide into a first part of the target population of cells, e.g. by transfection or microinjection; expressing the encoding polynucleotide to produce the fusion polypeptide, thereby to cause it to be exported from said first part of said target population, and to cause it to be taken up by a second part of the target population of cells not directly producing the fusion polypeptide.

Coupling products (including chemically coupled products) can also be transported into a target population of cells by directly exposing the cells to a preparation of the coupling products, thereby to cause the target cells to take them up.

In this specification, 'VP22' denotes: protein VP22 of HSV, e.g. of HSV1, and transport-active fragments and homologues thereof, including transport-active homologues from other herpesviruses including varicella zoster virus VZV, equine herpesvirus EHV and bovine herpesvirus BHV; modified and mutant proteins and fusion polypeptides and coupling products having homology therewith and a transport function corresponding to a transport function of VF22 of HSV1; and in context also relates to nucleic acid sequences encoding any of the above whether in the form of naked DNA or RNA or of a vector, or of larger nucleic acid sequences including such sequences as sub-sequences.

Among sub-sequences of herpesviral VP22 protein with transport activity we have found that for example transport activity is present in polypeptides corresponding to aminoacids 60–301 and 159–301 of the full HSV1 VP22 sequence (1–301). For the sequence, see e.g. FIG. 4 in WO 97/05265. A polypeptide consisting of aa 175–301 of the VP22 sequence has markedly less transport activity, and is less preferred in connection with the present invention. Accordingly, the present invention relates in one aspect to coupled and fusion proteins comprising a sub-sequence of VP22 containing a sequence starting preferably from about aa 159 (or earlier, towards the N-terminal, in the native VP22 sequence), to about aa301, and having (relative to the full VP22 sequence) at least one deletion of at least part of the VP22 sequence which can extend for example from the N-terminal to the cited starting point, e.g. a deletion of all or part of the sequence of about aa 1–158. (Less preferably, such a deletion can extend further in the C-terminal direction, e.g. to about aa 175.) For example, partial sequences in the range from about aa 60–301 to about aa 159–301 are provided.

VP22 sequences as contemplated herein extend to homologous proteins and fragments based on sequences of VP22 protein homologues from other herpesviruses, e.g. the invention provides corresponding derivatives and uses of the known VP22-homologue sequences from VZV (e.g. all or homologous parts of the sequence from aa 1–302), from MDV (e.g. all or homologous parts of the sequence from aa 1–249) and from BHV (e.g. all or homologous parts of the sequence from aa 1–258). The sequences of the corresponding proteins from HSV2, VZV, SHV and MDV are available in public protein/nucleic acid sequence databases. Thus, for example, within the EMBL/Genbank database, a VP22 sequence from HSV2 is available as gene item UL49 under accession no. Z86099 containing the complete genome of HSV2 strain HG52; the complete genome of VZV including the homologous gene/protein is available under accession numbers X04370, M14891. M16612; the corresponding protein sequence from BHV is available as 'bovine herpesvirus 1 virion tegument protein' under accession number U21137; and the corresponding sequence from MDV is available as gene item UL49 under accession number L10283 for 'gallid herpesvirus type 1 homologous sequence genes'. In these proteins, especially those from HSV2 and VZV, corresponding deletions can be made, e.g. of sequences homologous to aa 1–159 of VP22 from HSV1. These cited sequences are hereby incorporated herein by reference. Homologies between them are readily accessible by the use of standard algorithms and software, for example those mentioned in WO 95112673, page 9.

Furthermore, chimeric VP22 proteins and protein sequences are also useful within the context of the present invention, e.g. a protein sequence from VP22 of HSV1 for part of which a homologous sequence from the corresponding VP22 homologue of another herpesvirus has been substituted. For example, into the sequence of polypeptide 159–301 from VP22 of HSV1, C-terminal sequences can be substituted from VP22 of HSV2 or from the VP22 homologue of BHV.

It has been found that deletion of the 34-aminoacid C-terminal sequence from VP22 of HSV1 abolishes transport-activity, thus this sequence region contains essential elements for transport activity. According to a further aspect of the invention, there are provided coupled and fusion polypeptides comprising. the 34-aminoacid C-terminal sequence from VP22, or a variant thereof, together with a sequence from another protein selected from: (a) proteins for cell cycle control; (b) proteins that are conditionally cytotoxic or lethal upon administration (to a cell containing them) of a corresponding drug or activator compound; (c) entigenic sequences or antigenic proteins (e.g. of greater than 12 aminoacid residues in length) from microbial and viral antigens and tumour antigens; (d) immunomodulating proteins; and (e) therapeutic proteins. These are provided for example for use by administration in the form of protein to cells that will take them up. Coupled products of modified terminal fragments having at least one mutation insertion or deletion relative to the C-terminal 34 aminoacid sequence of HSV1 VP22 are also provided.

It has also been found that sequences necessary for transport activity contain one or a plurality of aminoacid sequence motifs or their homologues from the C-terminal sequence of VP22 of HSV1 or other herpesviruses, which can be selected from RSASR SEQ ID NO:1, RTASR SEQ ID NO:3, RSRAR SEQ ID NO:5, RTRAR SEQ ID NO:7, ATATR SEQ ID NO:9, and wherein the third or fourth residue A can be duplicated, e.g. as in RSAASR SEQ ID NO:2 and SEQ ID NOS:4, 6, 8, 10. Corresponding fusion polypeptides with proteins of the kinds mentioned herein are also provided.

In addition to their uses as indicated elsewhere herein, the coupled and fusion polypeptides can also be used to raise antibodies which can be used in diagnostic and monitoring specific binding assays in per-se known manner, e.g for monitoring the intracellular localization of the coupled or fusion proteins themselves or their components.

('VP22' herein is not intended to include natural unmodified VP22 protein or corresponding gene in its natural and unmodified association with herpes virus in its various natural lifecycle stages, e.g. in association with herpesvirus which has not been subjected to genomic alteration. However, 'VP22' does for example refer to the corresponding protein or gene of a virus which has for example been altered in respect of its UL49/VP22 gene or function, or which has had inserted into its genome an additional and/or hybrid VP22 gene.)

The coupling products or fusion proteins based on VP22 can have a range of molecular sizes. The products can in practice be for example up to about 70 kDa or more, e.g. 90 kDa or 100 kDa or more in respect of the size of the protein to be coupled or fused to VP22. The embodiments of the invention include examples where the fusion peptide is e.g. at least about 13 residues long, or more than about 12 aminoacid residues long, e.g. other than a 12-residue antigenic epitope peptide. The proteins to be fused can sometimes also be more than about 27 or 32 kDa. e.g. they can be other than 27 kDa in size. For example, one of the proteins that can be thus coupled, p53. itself has a size of about 53 kDa. The coupled polypeptide or fusion protein, including the VP22 component can have a size up to about 120 kDa, e.g. up to about 80 kDa or 100 kDa.

It is sometimes preferred that the VP22 sequence is fused at its N-terrninus to the sequence of the chosen other protein of one of the kinds mentioned herein. C-terminal fusions can sometimes be correspondingly less preferred.

In the polypeptides of the invention, mutations of the constituent aminoacid sequences (including those of the immunomodulatory and other proteins mentioned herein) can be incorporated in the fusion polypeptides and other coupled proteins. Included here are proteins having mutated sequences such that they remain homologous, e.g. in sequence, function, and antigenic character or other function, with a protein having the corresponding parent sequence. Such mutations can preferably for example be mutations involving conservative aminoacid changes. e.g. changes between aminoacids of broadly similar molecular properties. For example, interchanges within the aliphatic group alanine, valine, leucine and isoleucine can be considered as conservative. Sometimes substitution of glycine for one of these can also be considered conservative. Interchanges within the aliphatic group aspartate and glutamate can also be considered as conservative. Interchanges within the amide group asparagine and glutamine can also be considered as conservative. Interchanges within the hydroxy group serine and threonine can also be considered as conservative. Interchanges within the aromatic group phenylaalanine, tyrosine and tryptophan can also be considered as conservative. Interchanges within the basic group lysine, arginine and histidine can also be considered conservative. Interchanges within the sulphur-containing group methionine and cysteine can also be considered conservative. Sometimes substitution within the group methionine and leucine can also be considered conservative. Preferred conservative substitution groups are aspartate-glutamate; asparagine-glutamine; valine-leucine-isoleucine; alanine-valine; phenylalanine- tyrosine; and lysine-arginine. In other respects, mutated sequences can comprise insertion and/or deletions. The mutated protein sequences can additionally or alternatively be encoded by polynucleotides that hybridize under stringent conditions with the appropriate strand of the naturally-occurring polynucteotide encoding the parent protein, and can be tested for positive results in known functional tests relevant to the parent protein. ('Stringent conditions' are sequence dependent and will be different in different circumstances. Generally, stringent conditions can be selected to be about 5 deg C. lower than the thermal melting point (Tm) for the specific sequence at a defined ionic strength and pH. The Tm is the temperature (under defined ionic strength and Ph) at which 50% of the target sequence hybridizes to a perfectly matched probe. Typically, stringent conditions will be those in which the salt concentration is at least about 0.02 molar at pH 7 and the temperature is at least about 60 deg C. As other factors may affect the stringency of hybridization, including, among others, base composition and size of the complementary strands, the presence of organic solvents and the extent of base mismatching, the combination of parameters is more important than the absolute measure of any one.)

Coupling with cell cycle control proteins:

In one useful class of embodiments of the invention, VP22 can be coupled with per-se known cell cycle control proteins. Thus, in an example of the invention concerned with cell cycle control, as particularly described in an example below, VP22 can be coupled with p53 protein. A purpose and use here can be to block cell cycle progression, especially in malignant cells.

VP22 can also usefully be coupled with cyclin-dependent kinase inhibitors, e.g. p16, p21 or p27. Normal cell cycle progression requires these proteins; absence of these can derepress the cell cycle, and corresponding coupling products can be used for treatment of cancer cells.

VFP22 coupling products can also usefully be used in the modulation of apoptosis, e.g. to induce cell death, of the apoptosis type, by the introduction into a cell of a protein apoptotic domain coupled to VP22, such as e.g. apoptosis protein bax, or its known identified apoptotis inducing peptide; or known related protein bad or bak. Here too the coupling product can be applied in the form either of protein or DNA encoding it. VP22 coupling products can be used in the form of VP22 with known proteins of the bcl2 family, such as bcl2 itself, bcl-xL, or bclw, to mask or inhibit apoptosis where this is desired, e.g. in treatment of neurodegeneration.

Other VP22 coupling products can be used to promote apoptosis, comprising VP22 linked with known ICE-like proteases. VP22 linkage products with inhibitors of ICE-like proteases, eg pseudosubstrates, can be used to mask or overcome the apoptosis-stimulating effects the proteases themselves.

Thus, according to an embodiment of the invention there is provided a fusion polypeptide comprising an aminoacid sequence with the transport function of herpesviral VP22 protein and a sequence with the cell cycle control functionality of p53 protein. The fusion polypeptide can include for example substantially the full length p53 sequence or substantially the full length VP22 sequence, or both.

Fusion with VP22 can thus be used for delivery of an agent for cell cycle control such as p53. (Where the description given herein refers to p53 and related peptides, it will be understood that, where the context admits, alternative cell cycle control agents, such as for example those p53 analogues and other cell cycle control proteins mentioned and referred to herein, are also contemplated, as are, more generally, alternative fusion or coupling partners for VP22, of any of the other types mentioned herein.) Once expressed in a subpopulation of expressing cells, such a fusion protein can be transported by the VP22 transport mechanism from the expressing cell into a significant proportion of surrounding cells, and the foreign attached polypeptide can then exert its functionality.

Also provided by this aspect of the invention are corresponding polynucleotides, encoding a fusion polypeptide that comprises a sequence with the transport function of herpesviral VP22 protein and a sequence with the human/mammalian cell cycle-regulating function of p53 protein. The polynucleotide can be comprised in an open reading frame operably linked to a suitable promoter sequence.

The polynucleotide can according to examples of the invention form part of an expression vector, e.g. comprising the polynucleotide carried in a plasmid. The expression vector can be for example a virus vector or a non-viral transfection vector. The vectors can for example be analogues or examples of those described and referred to in WO 97/05265 or Elliott and O'Hare (1997).

Also provided by the invention are methods of inhibiting cell division, which comprise exposing cells that have insufficient active/free p53 to arrest their cell cycle, to contact with a fusion polypeptide as described herein.

Among the methods of the invention is a method of inhibiting tumour cell division, which comprises exposing a tumour cell present in a tumour cell mass, the tumour cell comprising insufficient active/free p53 to arrest its cell cycle, to contact with a vector as described herein, thereby causing the cell to express a fusion polypeptide as described herein and to expose other cells of the tumour cell mass to contact with the fusion polypeptide.

We have shown (see description below) that VP22-p53 can be transported to many untransfected cells in a monolayer. The fusion protein can be functional in cell cycle arrest and/or induction of apoptosis, for example both in primary expressing cells and in cells which have received VP22 via cell-to-cell spread. For example, the fusion protein can be applied to a p53 negative osteosarcoma cell line SAOS-2 (Diller et al., 1990). Functional p53 expressed in these cells causes cell cycle arrest at the $G_1$-S boundary and ultimately cell death, this can be assayed using confocal microscopy and antibodies against specific cell cycle markers. Function of the p53 fusion protein can also be used and assessed in other tumorigenic cell fines where p53 is present but contains specific and well characterized point mutations leading to non-functionality.

A number of vector systems such as retroviral or adenoviral infection or the injection of protein-liposome complexes can be readily adapted to form examples of this invention for the administration of cell-cycle control proteins to cells and tissues of human and non-human animal subjects to be treated. For example, in relation to work on p53 protein alone, these have clearly demonstrated that addition of wild type p53 protein can curtail cancerous cell growth in vivo. A number of therapeutic applications of non-invasive delivery of VP22 coupling products with celleycle control proteins will be apparent to the skilled reader.

For example, naked DNA for a VP22-protein fusion with a tumour effector protein such as p53 can be injected into a tumour, e.g. a solid tumour, e.g. a solid tumor selected by molecular diagnostics for lack of functional p53.

Recombinant viruses can be used as mentioned, encoding and able to express VP22-p53 and equivalently-functioning fusion proteins. For example an adenovirus can express VP22-p53 and can be made dependent on a tumour-specific promoter to drive an essential viral gene such as E1a. More generally, a recombinant virus vector carrying such a fusion can be defective, non-replicating or replication-restricted so that replication is dependent on conditions prevailing in the target tissue or cell but not in normal or non-target cells.

In certain examples of the invention, the protein having p53 functionality can for example comprise variants or mutants of p53, for example those variants as described in specification WO 97/04092 (Rhone Poulenc Rorer SA: Bracco L., Conseiller E.) ("New p53 variants e.g. with oligomerisation domain replaced by leucine zipper—useful for treating hyper-proliferative disorders, especially cancer and restenosis"), which describes inter alia the following variant proteins: (a) variants of protein p53 having at least part of the oligomerisation domain deleted and replaced by a leucine zipper domain; (b) variants of p53 preferentially active in transformed cells, where all or part of at least one functional domain has been deleted and replaced by a heterologous domain preferentially active in such cells; (c) variants of p53 with a deletion in the C-terminal part, from residue 366, followed by a 19 amino acid sequence (encoded by a 76 bp fragment reproduced in the specification) representing the last part of the alternatively spliced part of nurine p53; and (d) chimeric protein containing a transactivating domain, a DNA-binding domain, a nuclear localisation domain and an oligomerisation domain, in which DNA-binding domain and the nuclear localisation domain comprise amino acids 75-325 6r 75–336 of human wild-type p53.

In further examples of the invention, vectors and fusion proteins can encode or comprise variant p53 polypeptides comprising chimaeric p53 sequences including heterologous tetramerisation domains, which can be adapted from those described in specifications WO 96/16989 and U.S. Pat. No. 5,573.925 (Wistar Institute of Anatomy & Biology: Halazonetis TD) and used in corresponding ways. In such examples of the invention, the p53 sequences can comprise chimaeric p53 protein having a native p53 sequence and a heterologous tetramerisation domain that forms homotetramers such that the resulting chimaeric protein cannot hetero-oligomerise with wild-type or tumour derived mutant p53 and does not interfere with the native p53 tumour suppressing functionality.

Fusion proteins and vectors according to further examples of the present invention can be used for treatment of hyperproliferative disease, especially cancer and autoimmune disease, e.g. restenosis, and particularly for treatment of cells having a p53 mutation and which also express protein MDM2 at high level, including for example HPV-related cancer cells. They may also be used to kill hyperproliferating cells in vitro. Such variants can involve active and stable tumour suppressors and apoptosis-inducing agents and are proposed to be active where the wild type protein is not, i.e. not inactivated by dominant negative or oncogenic mutants, nor by other cellular proteins (because the leucine zipper domain prevents formation of inactive mixed oligomers).

Fusion proteins and vectors can also be used, according to further examples of the present invention, in medicaments for suppressing neoplastic phenotype of cancer cells lacking wild-type p53 protein, in ways e.g. corresponding to the use of wild-type p35 gene as described in specification EP 0 710 722 (Univ Califomia: Chen P., Lee W.), which describes genes and retroviral vectors for the purposes inter alia of suppressing neoplastic phenotype in cancer cells such as osteosarcoma cells, lung carcinoma cells, colon carcinoma cells, lymphoma cells, leukemia cells, soft tissue sarcoma cells or breast, bladder or prostate carcinoma cells.

Fusion proteins and vectors can also be used according to further examples of the present invention. e.g. in ways corresponding to those described in specification WO 95/12660 (Univ Texas System: Roth J. A. et al), which describes recombinant adenovirus which carries an adenovirus vector construct comprising an expression region encoding p53. and which is capable of expressing the p53 in for example human malignant cells, and which can be used inter alia for regional delivery of tumour suppressor gene p53, to diseased cells, either to restore p53 function to p53 deficient cells, or to suppress tumour growth in cells having abnormal p53. and thus to treat human malignancies such as breast and lung cancer. Such adenovirus may also be used for in vitro analyses and mutagenesis studies of various p53 genes.

Fusion proteins and vectors can also be used, according to further examples of the present invention as inhibitors of hepatitis B virus (HBV) replication, in ways corresponding to those described in U.S. Pat. No. 5,635,473 and WO 96/11017 (Mogam Biotechnology Research Institute: H. S. Lee et al).

Screening assays for identifying agents that effectively increase the level of cell death, and which can act as p53 analogues and can induce apoptosis in cells, are described for example in U.S. Pat. No. 5,484,710 (La Jolla: J. C. Reed et al), particularly in example IV thereof. Also contemplated as alternative embodiments of the invention are fusion proteins and related materials incorporating VP22 functionality and Bax protein functionality. In relation to Bax protein, reference is made to U.S. Pat. No. 5,484,710 and references cited therein, incorporated herein by reference.

Coupling with 'suicide protein':

In a further class of embodiments of the invention, VP22 or a functional sub-sequence thereof can be usefully coupled or fused with for example a 'suicide protein' such as for example the known thymidine kinase, nitroreductase, or other enzyme or functional fragment thereof known as applicable for a similar purpose. The coupling product can penetrate into cells which are to be treated with (in the case of thymidine kinase) ganciclovir or another drug (prodrug) of the same family, so that the prodrug is converted in the cells containing the 'suicide gene' product to an active form to kill the cells.

Suitable examples of useful known suicide genes and corresponding pro-drugs are given and referred to for example in WO 94/13824 (Univ Curie Paris, M. Caruso et al), in WO 95/05835 (Baylor College: S. Chen et al), and in WO 93/08288 (Cancer Research Campaign Technology: G. Anzelark et al), and WO 93/01281 (US DHHS: R. M. Blaese et al), and include, besides thymidine kinase (suicide gene) and ganciclovir/acyclovir (prodrug), nitroreductase (suicide gene) and CB1954 (prodrug), and cytosine deaminase (suicide gene) and 5-fluorocytosine (prodrug). These and other suicide proteins and corresponding (pro)drugs are also reviewed and their uses mentioned in 'Genetic Prodrug Activation Therapy', A. Rigg and K. Sikora, *Molecular Medicine Today,* Aug 1997, pp 359–366.

Where the VP22-TK fusion is presented in the form of DNA in any of the ways described in WO 97/05265 or Elliott and O'Hare (1997). a target cell can be transfected with the gene encoding this fusion, and the expressed fusion can then be translocated out of the cell in which it was expressed and into surrounding cells—producing a killing effect on such cells when treated with ganciclovir etc, an effect which is different from, and can be additional to known bystander effects. Alternatively, as with other embodiments, such a VP22-TK fusion can be applied directly as protein.

Coupling with antigens:

In further embodiments, the invention concerns for example transport proteins related to VP22 or its active fragments fused in fusion polypeptides or otherwise coupled with antigenic sequences or proteins (e.g. of greater than 12 aminoacid residues in length) selected for example from any of the antigenic materials or other proteins and peptides mentioned below.

In addition to the fusion polypeptides and coupling products, the invention provides coupling hybrids comprising VP22 coupled to a DNA that can for example comprise suitable known regulatory elements so that it can be transcribed and translated, and containing an open reading frame encoding any of the proteins mentioned below.

Coupling with antigens- VP22 can usefully be coupled with examples of microbial and viral antigens and of tumour antigens such as those mentioned below.

Treatment with coupling products of VP22 involving antigens of pathogens as provided hereby can evoke useful immune response against corresponding pathogens. Examples of such antigens are papilloma virus proteins L1 and L2. HIV proteins, gag, pot, env and nef, chlamydia antigens (such as the chiamydia Major Outer Membrane Protein MOMP) and Chlamydia heat shock proteins.

VP22 can also usefully be coupled with antigens from mycobacteria such as antigen from Mycobacteriurn tuberculosis.

Alternatively the antigen can be a tumour associated antigen, whereby the anti- tumour activity of the CTLs associated with tumour cell depletion is enhanced. It has been found that specific cytokines such as tumour necrosis factor-$\alpha$, interferon gamma, interleukin-2, interieukin-4 and interleukin-7 are particularly useful in this regard. Tumour associated antigens and their role in the immunobiology of certain cancers is discussed for example by P. van der Bruggen et al., *Current Opinion in Immunology,* 4(5) (1992) 608–612. Particular examples of such antigens which are envisaged for use in the context of the present application are E6 and E7 antigens of human papillomavirus (especially for example of types 6, 11, 16, 18, etc); Epstein-Barr virus-derived proteins, e.g. those identified in references 24 and 25 in P. van der Bruggen et al., cited above: antigens of the MAGE series as identified in T. Boon. *Adv Cancer Res* 58 (1992) pp 177–210 and/or MZ2-E and other antigens as identified in P. van der Bruggen et al, *Science* 254 (1991) 1643–1647; melanoma proteins, e.g. human tyrosinase: and mucins such as those identified in P. O. Livingston, in *Current Opinion in Immunology* 4 (5) (1992) pp 624–629: e.g. MUC1 as identified in J. Burchell et al, *Int J Cancer* 44 (1989) pp 691–696.

VP22 can also be usefully coupled with viral proteins such as glycoprotein antigens, e.g. from herpesviruses, such as gH or gD or gB of herpes simplex virus; or gp50 of pseudorabies virus, as an example of an antigen of a veterinary pathogen, in this case a veterinary virus.

VP22 thus can be usefully coupled with antigens known from the prior art of malignant tumour treatment, including studies that have highlighted the potential for therapeutic vaccination against tumours using autologous material derived from a patient's own tumour. The theory behind this approach is that tumour cells may express one or more proteins or other biological macromolecules that are distinct from normal healthy cells, and which might therefore be used to target an immune response to recognise and destroy the tumour cells.

These tumour targets may be present ubiquitously in tumours of a certain type. A good example of this in cervical cancer, where the great majority of tumours express the human papillomavirus E6 and E7 proteins. In this case the tumour target is not a self protein, and hence its potential as a unique tumour-specific marker for cancer immunotherapy is clear.

There is increasing evidence that certain self proteins can also be used as tumour target antigens. This is based on the observation that they are expressed consistently in tumour cells, but not in normal healthy cells. Examples of these include the MAGE family of proteins. It is expected that more self proteins useful as tumour targets remain to be identified.

Tumour associated antigens and their role in the immunobiology of certain cancers are discussed for example by P. van der Bruggen et al, in *Current Opinion in Immunology*, 4(5) (1992) 608–612. Other such antigens, of the MAGE series, are identified in T. Boon, *Adv Cancer Res* 58 (1992) pp 177–210. and MZ2-E and other related tumour antigens are identified in P. van der Bruggen et al, *Science* 254 (1991) 1643–1647: tumour-associated mucins are mentioned in P. O. Livingston, in *Current Opinion in Immunology* 4 (5) (1992). pp 624–629: e.g. MUC1 as mentioned in J. Burchell et al, *Int J Cancer* 44 (1989) pp 691–696.

Coupling with immunomodulating proteins:

Embodiments of the invention of use in immune modulation include for example the following. VP22 can usefully be coupled with examples of cytokines or of other immunomodulatory compounds as mentioned below. Thus, VP22 can also be usefully coupled with immuno modulating proteins, e.g. those which enhance the immune response including the cytokine, interleukin 1, interleukin 2 and granulocyte-macrophage colony stimulating factor (GM-CSF). Such products can for example be used in ways analogous to those mentioned in for example WO 96/26267 or WO 97/14808, to alter, e.g. to increase, an immune reponse specific to a target cell type, e.g. a tumour cell type, which has been exposed to the product either in-vitro or in-vivo.

As used herein, the expression "immunomodulatory protein" and related terms includes a protein or proteins which either enhance or suppress a host immune response to a mutant virus or protein encoded thereby, or to an antigen such as an immunogen from a pathogen or source exogenous to the virus, or a tumour-associated antigen. The immunomodulating proteins are not normally those proteins presently used as immunogens (antigens) in themselves. An immunomodulatory protein can be a natural member of a human or non human animal immune system, e.g. of a mammalian immune system, with a functional binding capacity for another natural constituent of such an immune system. Alteratively an immunomodulatory protein can be a protein encoded by a pathogen, which has a functional binding capacity for a natural constituent of such an immune system.

Alternatively an immunomodulatory protein can be an artificial protein, for example a fragment of a natural immunomodulatory protein, or a mutein of such a protein or fragment, or a fusion protein incorporating any of these. Many immunomodulatory proteins, and genetic materials encoding them, and their nucleotide and aminoacid sequences, are known to the literature of this subject, and available in genetic sequence databases such as the EMBL database, and several are commercially available in the form of engineered genetic material for cloning and other manipulation.

Immunomodulating proteins coupled with VP22 as described herein can usefully for example be of sequences native to the species which is to receive treatment with these coupling products or with DNA e.g. in the form of recombinant viruses, e.g. an immunomodulating protein of human type for treatment of a human subject.

Examples of useful known immunomodulating proteins in this connection include cytokines, chemokines, complement components, immune system accessory and adhesion molecules and their receptors of human or non-human animal specificity. Useful examples include GM-CSF, IL-2, IL-12, lymphotactin, CD40, and CD40L. Further useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1 and MIP-1b, complement components and their receptors, or an accessory molecule such as B7.1, B7.2, ICAM-1, 2 or 3 and cytokine receptors.

OX40 and OX40-ligand (OX4OL) (gp34) (see e.g. WO 95/12673, WO 95/21251 and WO 21915) are further useful examples of immunomodulatory proteins. Immunomodulatory proteins can for various purposes be of human or non-human animal specificity and can be represented for present purposes, as the case may be and as may be convenient, by extracellular domains and other fragments With the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can for example comprise more than one cytokine or a combination of cytokine(s) and accessory/adhesion molecule(s).

Immune response evoked by the use of such VP22 coupling products or by vectors encoding them can include immune responses of a variety of types, e.g. a response against a virally-encoded protein, and/or a response against a host antigen, being a response stimulated by a viral vector or by the expression of a heterologous gene encoded thereby, e.g. the coupling product with VP22. Among the uses of the mutant virus vectors as described herein is e.g. to protect a subject of a susceptible species against infection by a corresponding wild-type virus when the subject is treated therewith, e.g. infected therewith, e.g. by direct immunisation.

An immunomodulatory protein to be coupled with VP22 can be itself a hybrid or fusion protein which comprises a polypeptide region having homology to and functionality of an immunomodulatory protein, linked to a polypeptide region having another homology and optionally another functionality. For example, the immunomodulatory protein can be, comprise, or correspond in functionality to the gp34 protein identified as a binding partner to human Ox40 (see W. Godfrey et al, *J. Exp Med* 180(2) 1994 pp 757–762, and references cited therein, including S. Miura et al, *Mol Cell Biol* 11(3) 1991, pp 1313–1325). The version of this protein functionality that can be encoded in the mutant viral genome can correspond to the natural gp34 sequence itself, or to a fragment thereof, or to a hybrid expression product e.g. based on the (C terminal) extracellular (binding) domain of gp34 fused to another protein, e.g. to the constant region of an immunoglobulin heavy chain such as human IgG1, e g. with the extracellular domain of gp34 (a type 2 membrane protein) fused at its N-terminal to the C-terminal of the immunoglobulin constant domain.

Others of the immunomodulatory proteins can also be carried and expressed in such derivative and hybrid forms, including mutated forms as mentioned herein.

In certain examples the immunomodulating protein can comprise a cytokine, preferably granulocyte macrophage colony stimulating factor (GM-CSF), e.g. murine or preferably human GM-CSF.

Murine and human GM-CSFs are both known: the murine GM-CSF gene encodes a polypeptide of 141 amino acids, the mature secreted glycoprotein having a molecular weight of between 14 k–30 k daltons depending on the degree of glycosylation. GM-CSF generically is a member of the haematopoietic growth factor family and was first defined and identified by its ability to stimulate in vitro colony formation in haematopoietic progenitors. GM-CSF is a potent activator of neutrophils, eosinophils and macrophage-monocyte function, enhancing migration, phagocytosis, major histocompatibility complex (MHC) expression, and initiating a cascade of bioactive molecules which further stimulate the immune system. GM- CSF is currently being clinically evaluated for treatment of neutropenia following chemotherapy and as an adjuvant in cancer therapy.

The heterologous nucleotide sequence employed can comprise a heterologous gene, gene fragment or combination of genes provided it encodes an immunornodufating protein as defined above.

According to examples of the invention, combinations of two or more immunomodulatory proteins can be used for the purposes described herein. In particular examples, given for illustration only and not limitation, combinations involving IL2, GMCSF, lymphotactin andlor CD4OL can be used with each other or with others of the immunomodulatory proteins cited above. Each of the other binary combinations of the immunomodulatory proteins mentioned above are also given by, and within the scope of, this disclosure.

Other coupling products:

In certain embodiments the invention can be useful in gene therapy applications: thus for example, VP22 can also be usefully coupled with examples of genes used or proposed to be used in gene therapy including: the gene for human adenosine deaminase (ADA), as mentioned in for example WO 92/10564 (K. W. Culver et al: U.S. Secretary for Commerce & Cellco Inc), WO 89/12109 & EP 0 420 911 (I. H. Pastan et al): the cystic fibrosis gene and variants described in WO 91/02796 (L. C. Tsui et al: HSC Research & University of Michigan), in WO 92/05273 (F. S. Collins & J. M. Wilson: University of Michigan) and in WO 94/12649 (R. J. Gregory et al: Genzyme Corp).

VP22 can also usefully be coupled with known transcriptional regulatory proteins such as NF-AT, which becomes activated by translocation to the nucleus and induces transcription of interleukin e.g. of IL1. The coupling with VP22 can be used here to avoid retention of the coupled product in the cytoplasm.

The invention also includes coupled and fusion proteins in which a linker sequence is provided that enables the fusion protein to be split intracellularly to enable separation of the antigenic part, such as that mentioned above, from the transport protein part. A cleavage-inducing sequence can comprise for example the aminoacid sub-sequence RVCS-NPPCETHETGTTNTATATSN SEQ ID NO:11 or other cleavage sequences indicated for example in A. C. Wilson et al, in *Genes and Development* 9 (1995) 2445–2458.

Also provided by the present invention are processes for treating cells with coupling products as described herein, so as to produce immunogenic, immunomodulatory, cytotoxic/lethal or therapeutic effects.

Examples of materials and processes as described herein are useful in the modulation of cellular activity, e.g. with the aim and effect of producing or altering immune responses, for example for the prophylaxis or therapy of disease, e.g. the production of immune responses against pathogens or tumours.

Other uses for certain of the materials and processes hereof include the regulation of gene expression in cells, e.g. for purposes of corrective gene therapy and/or for reducing or controlling tumour cell growth and activity. Cell treatments according to the invention can be in-vitro, ex-vivo or in-vivo.

Among the derivatives of VP22 that can be used according to aspects of the invention as transport active substances and for coupling with materials to be transported, for the purposes set forth elsewhere herein, are peptides comprising a transport-active functional sequence from the C terminal section of VP22.

Non-limitative examples of treatment methods using the materials described herein comprise treatment of antigen-presenting cells or cell preparations containing them with a fusion of VP22 and an antigen, e.g. one of those antigens mentioned above, (or with a vector, e.g. a viral vector, encoding such a fusion), so as to procure processing of the antigen and presentation by the MHCI route so as to procure a CTL response to the antigen. The methods so provided include priming and expansion of T cells and adoptive immunotherapy using the materials so obtained, in a manner otherwise analogous to known priming, expansion and adoptive immunotherapy methods.

A number of vector systems such as retroviral or adenoviral infection or the injection of protein-liposome complexes, as well as herpesviral vector systems, can be readily adapted to form examples of this invention. For example, naked DNA for a VP22-protein fusion with a protein of one of the kinds mentioned herein can be injected into a tissue to be treated, according to the nature and purpose of the protein to be delivered. Recombinant viruses can be used as mentioned, encoding and able to express VP22 fusion proteins. A recombinant virus vector carrying such a fusion can be defective, non-replicating or replication-restricted so that replication is dependent an conditions prevailing in the target tissue or cell but not in normal or non-target cells.

Vectors and fusion proteins of examples of the invention can be useful in gene therapy, and to treat or protect against abnormal cell proliferation, esp. cancer but also psoriasis, atherosclerosis and arterial restenosis, and to induce apoptosis of e.g. proliferating lymphocytes, i.e. to induce tolerance, e.g. to prevent transplant rejection or for treatment of autoimmune diseases such as systemic lupus erythematosus or rheumatoid arthritis.

In addition to medical therapeutic applications, the effect shown herein can also be exploited by assays, provided by the invention, which rely on substrate-enzyme interactions or the interaction of proteins expressed in different cellular populations.

An embodiment of the invention is further described, without intent to limit the invention, with reference to the accompanying drawings and to the materials and methods described below.

In the accompanying drawings,

FIGS. 1(a)–1(h) illustrate that:

Mock-transfected cos-1 cells were labelled by indirect immunofluorescence with antibodies for VP22 (FIG. 1a), p53 (FIG. 1c) and the CMV epitope (FIG. 1d) to establish the levels of background label. Cells transfected with pc49epB (FIG. 1b) and labelled for VP22 demonstrate a typical VP22 cytoplasmic pattern with clear spread to the nuclei of adjacent cells. Cells transfected with the VP22-p53 fusion protein construct p4953ep+10 were labelled for VP22 and p53 (FIGS. 1e and 1f) or VP22 and epitope (FIGS. 1g and 1h): the fusion protein can be detected in the nuclei of cells adjacent to the primary expressing cell.

FIG. 3 illustrates that

Protein extracts from cos-1 cells transfected with a range of plasmid constructs were analysed by western blot. The panel shown leftmost has been probed with an antibody against VP22 and demonstrates that pUL49epB and pc4gepB plasmids encoding VP22 alone generate a protein of 33 kDa, the VP22-p53 fusion protein expressed from p4953ep+10 produces a protein of approx. 90 kDa with very little degradation.

The panel shown rightmost has been probed with an antibody against p53 and demonstrates that cells transfected with plasmids encoding either p53 alone (pcB6+p53) or the p4953ep+10 fusion protein construct produce p53 protein at 53 kDa. The p4953ep+10 construct also synthesises the VP22-p53 fusion protein at 90 kDa, the p53 in this sample may be a degradation product or more likely endogenously induced p53.

Materials and Methods
Cell culture and transfection

Cos-1 cells were grown in Dulbecco's modified MEM supplemented with 10% new born calf serum at 37° C. with 5% $CO_2$.

Transfections were performed using the BES/$CaCl_2$ method (Elliott and O'Hare. 1997) with 200 ng test plasmid with 1800 ng pUB19. Transfections were allowed to proceed for 48 h at which point the monolayers were harvested for immunofluarescence or western blot analysis.
Immunofluorescence and antibodies Cell monolayers on coverslips were fixed with 100% methanol for 15 mins at room temperature and labelled as described in Elliott and O'Hare (1997). All antibodies were diluted in PBS+10% serum. VP22 was detected using a rabbit polyclonal antibody AGV30 (1:500), p53 was detected using a mouse monoclonal antibody DO-1 (Santa-Cruz Ltd), the CMV epitope was detected using a mouse monoclonal antibody CMV LNA (Capricorn Ltd). Images were obtained using a Bio-Rad MRC600 confocal microscope.
Plasmid Constructs The VP22-p53 fusion protein construct was generated by cloning a full length p53 PCR fragment C-terminal to VP22 into a unique Bam site, keeping both VP22 and the CMV epitope in frame.
Western blot analysis Western blots were probed with anti-VP22 (1:10,000), anti-p53,(1:1000).

Figure 1E:
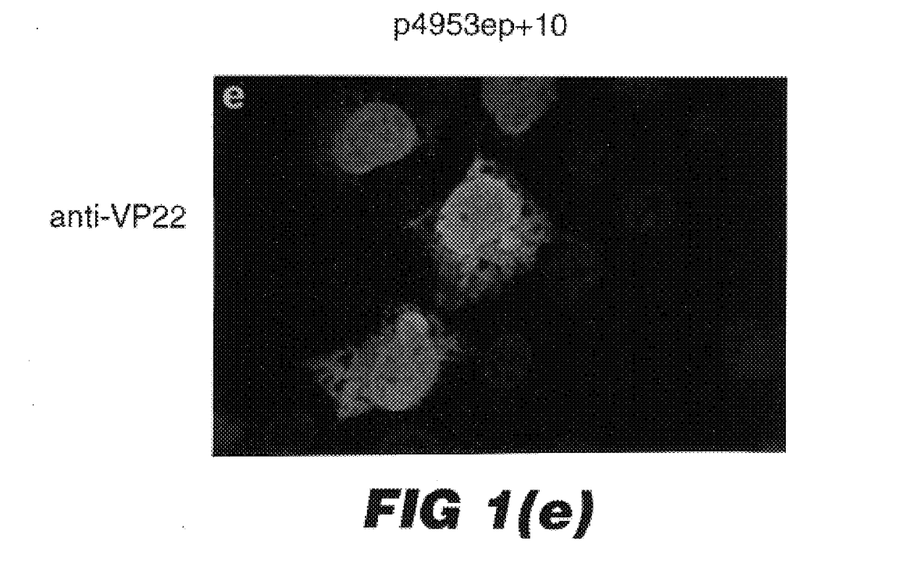
Figure 1F:
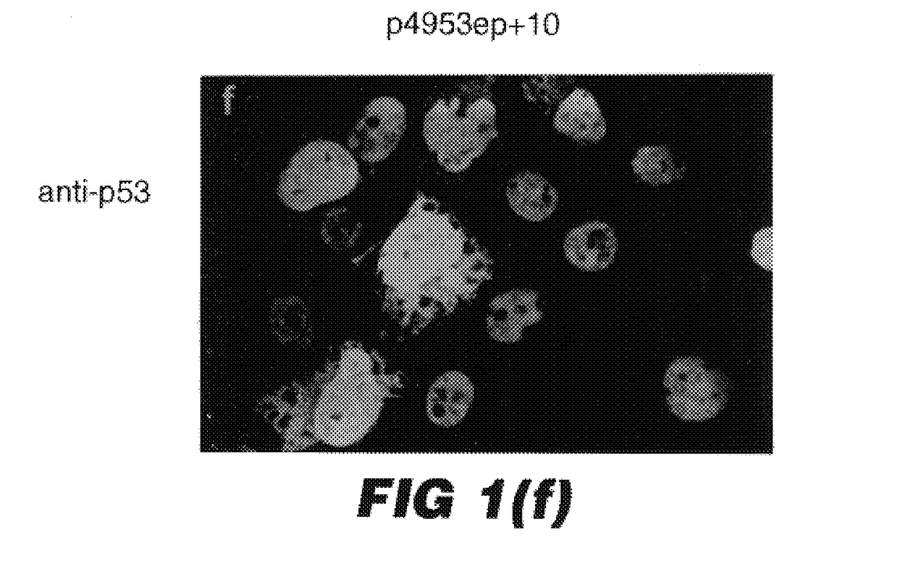
Figure 1G:
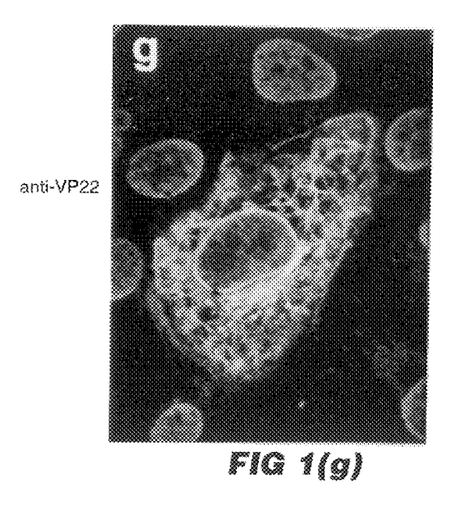
Figure 1H:
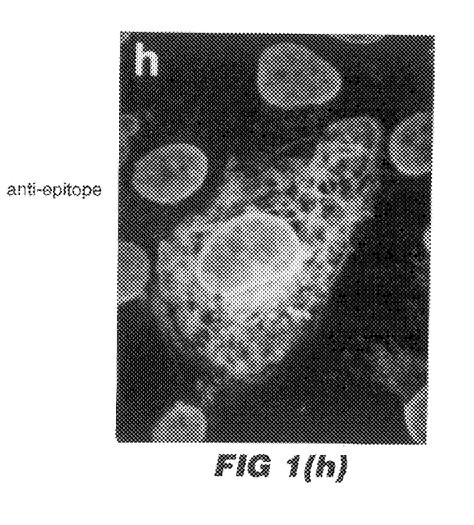
Figure 2:
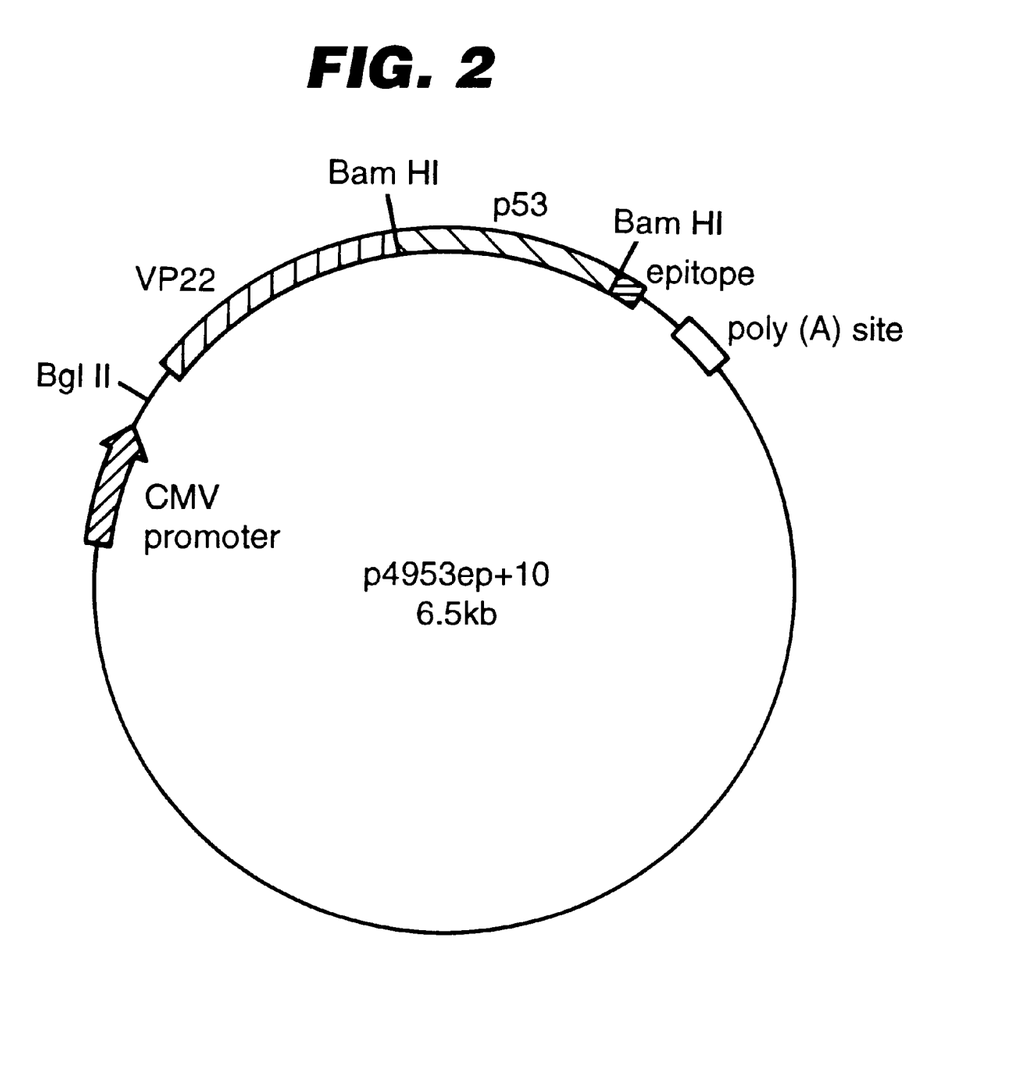
FIG. 2 is a plasmid map to illustrate p4953ep+10, encoding a fusion protein comprising sequences VP22, p53 and an epitope tag.
Figure 3:
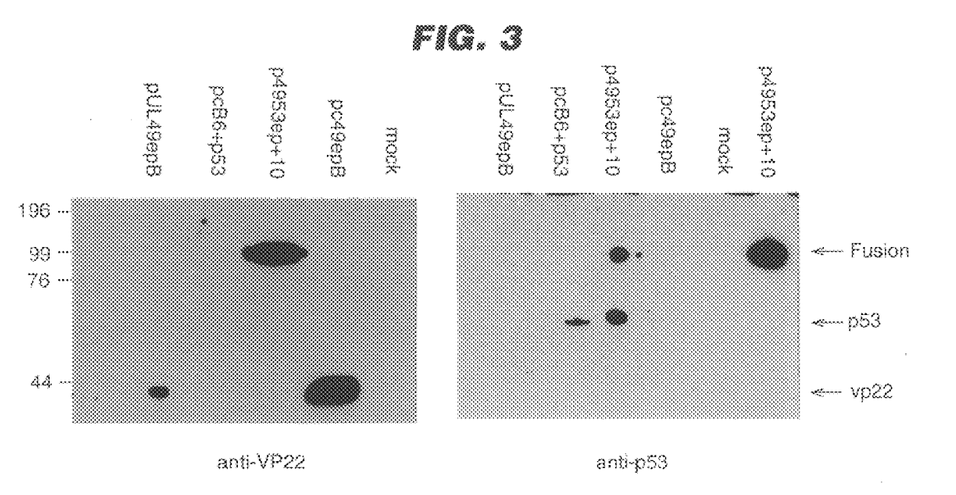

We constructed an epitope-tagged full length in-frame VP22-p53 fusion protein construct (FIG. 2). This vecor generates a fusion protein of approx 90 kDa when expressed in Cos-1 cells, with very little protein degradation as judged by western blot analysis (FIG. 3). When tested for delivery by intercellular trafficking, the fusion protein appears to function exactly as VP22 alone. It is located in the cytoplasm of primary transfected cells as shown by immunofluorescence using methanol-fixed Cos-1 cell monolayers labelled with anti-VP22 (FIGS. 1e and 1g), -p53 (FIG. 1f) or -epitope (FIG. 1h) antibodies and is able to move very efficiently into the nuclei of neighbouring cells. The relative efficiency of transport has not been empirically determined but appears only slightly less than VP22 alone.

In further experiments, p53-negative osteosarcomna cells were transfected (using the calcium phosphate technique) with naked DNA expressibly encoding either (a) wild-type VP22, (b) wild-type p53) or (c) the VP22-p53 fusion protein described above. The transfected cells (b) and (c) showed ability to undergo apoptosis, unlike the control cells (a), indicating that the VP22-p53 fusion protein retains the functionality of p53.

In variants of the example given here, VP22 deletion constructs with decreased fusion protein size can be made if desired, e.g. to improve rate or extent of transport, and without loss of protein function.

In further variants, the order of the components of the fusion can be varied, e.g. the p53 and VP22 sequences can readily be included in the order opposite to the order involved in the plasmid shown in FIG. 2, with satisfactory results.

The present disclosure extends to modifications and variations of the description given herein inclusive of the attached claims that will be apparent to the reader skilled in the art. The disclosure hereof, incorporating WO 97/05265 and of Elliott and O'Hare (1997) which are made an integral part hereof, is intended to extend in particular to classes and subclasses of the products and generally to combinations and to subcombinations of the features mentioned, described and referred to in the disclosure. Documents cited herein, including the references below, are hereby incorporated in their entirety by reference for all purposes.
Additional References Diller, L., Kassel, J. Nelson, C. E., Gryka, M. A., Litwak, G. Gebhardt, M. Bressac, B., Ozturk, M., Baker, S. J., Vogelstein, B. and S. H. Friend, (1990) p53 functions as a cell cycle control protein in osteosarcomas. *Mol. Cell. Bio.* 10:5772–5781.

Elliott G. and P. O'Hare (1997) Intercellular trafficking and protein delivery by a herpesvirus structural protein. *Cell* 88:223–233.

Ensoli, B.. Buonaguro, L., Barillari, G., Fiorelli, V., Gendelman, R., Morgan, R. A., Wingfield, P. and R. C. Gallo. (1993) Release, uptake and effects of extracellular human immunodeficiency virus Tat protein on cell growth and viral transactivation. *J. Virol.* 67:277–287.

Fawell, S., Seery, J., Daikh, Y., Moore, C., Chen, L. L., Pepinsky, B. and J. Barsoum. (1994) Tat-mediated delivery of heterologous proteins into cells. *Proc. Natl. Acad. Sci* 91:664–668.

Hamada, K., Alemany, R., Zhang, W. W., Hittelman, W. N., Lotan, R., Roth, J. A. and M. F. Mitchell. (1996) Adenovirus-mediated transfer of a wild-type p53 gene and induction of apoptosis in cervical cancer. *Cancer Research* 56:3047–3054.

Jackson, A., Friedman, S., Zhan, X., Engleka, K. A., Forough R. and T. Maciag. (1992) Heat shock induces the release of fibroblast growth factor 1 from NIH3T3 cells. *Proc. Natl. Acad. Sci.* 89:10691–10695.

Kumar, X. M., Srinivas, S., Detolla, L. J., Yu S. F., Stass, S. A. and A. J. Mixson. (1997) Parenteral gene therapy with p53 inhibits human breast cancer tumors in vivo through a bystander effect without evidence of toxicity. *Hum Gene Therapy* 6:177–185.

Levine, A. J. (1997) p53. the cellular gatekeeper for growth and division. *Cell* 88:323–331.

Nielsen, L. L., Dell, J., Maxwell, E., Armstrong, L., Maneval, D. and J. J. Catino. (1997) Efficacy of p53 adenovirus-mediated gene therapy against human breast cancer xenografts. *Cancer Gene Therapy* 4:129–138.

Sandig, V., Brand, K., Herwig, S., Lukas, J., Bartek, J. and M. Strauss. (1997) Adenovirally transferred p16 and p53 genes cooperate to induce apoptotic tumor cell death. *Nature Med.* 3:313–319.

Zheng, P. S., Iwasaka, T., Ouchida, M., Fukuda, K., Yokoyama, M. and H. Sugimori. (1996) Growth suppression of a cervical cancer cell line (TMCC1) by the human wild type p53 gene. *Gynecol Oncol.* 60:245–250.

We claim:

1. A fusion polypeptide comprising first and second amino acid sequences, wherein the first amino acid sequence comprises a herpesvirus VP22 protein or a fragment thereof that retains a herpesvirus VP22 protein transport function and the second amino acid sequence comprises a protein selected from the group consisting of:
   (a) proteins for cell cycle control;
   (b) suicide proteins;
   (c) immunomodulating proteins;
   (d) therapeutic proteins; and
   (e) fragments of (a)–(d) that retain one or more functions of that protein.

2. A polypeptide according to claim 1 wherein the second amino acid sequence is a mammalian cell cycle control protein.

3. A polypeptide according to claim 2 wherein the second amino acid sequence is a mammalian protein for increasing or inducing cell apoptosis or for conferring on a cell the ability to undergo apoptosis.

4. A polypeptide according to claim 2 wherein the second amino acid sequence is a mammalian cell cycle control protein selected from the group consisting of p53 proteins, cyclin dependent kinase inhibitors, and proteins of the bcl2 and bax families.

5. A polypeptide according to claim 4 wherein the second amino acid sequence comprises a p53 protein.

6. A polypeptide according to claim 5, wherein the first amino acid sequence is a full length VP22 sequence and the second amino acid sequence is a full length p53 sequence.

7. A polypeptide according to claim 1 wherein the second amino acid sequence is a suicide protein.

8. A polypeptide according to claim 7 wherein said suicide protein is selected from thymidine kinase and nitroreductase.

9. A polypeptide according to claim 7, wherein the first amino acid sequence is a full length VP22 sequence.

10. A polypeptide according to claim 1, wherein the first and second amino acid sequences are joined by a cleavage-inducing linker sequence.

11. A polypeptide according to claim 1, wherein the fragment of the herpesvirus VP22 comprises from about amino acid 159 to about amino acid 301 of the HSV VP22 protein.

12. A polypeptide according to claim 1, wherein the fragment of the herpesvirus VP22 comprises a sequence selected from the group consisting of
   (a) from about amino acid 60 to about amino acid 301 and
   (b) from about amino acid 159 to about amino acid 301 of the full length HSV VP22 sequence.

13. A polynucleotide encoding a polypeptide according to claim 1.

14. A vector comprising a polynucleotide according to claim 13.

15. A host cell comprising a vector according to claim 14.

16. A method of transporting a first polypeptide into a cell population, comprising exposing the cells to a fusion polypeptide comprising
   (a) the first polypeptide; and
   (b) a second polypeptide comprising a herpesvirus VP22 protein or a fragment thereof that retains a herpesvirus VP22 protein transport function.

17. The method of claim 16 wherein the first polypeptide is selected from the group consisting of
   (a) proteins for cell cycle control;
   (b) suicide proteins;
   (c) immunomodulating proteins;
   (d) therapeutic proteins; and
   (e) fragments of (a)–(d) that retain one or more functions of that protein.

18. The polypeptide of claim 1 wherein the first amino acid sequence comprises a HSV VP22 protein or a fragment thereof that retains a HSV VP22 protein transport function.

19. The method of claim 16 wherein the second polypeptide comprises a HSV VP22 protein or a fragment thereof that retains a HSV VP22 protein transport function.

* * * * *

UNITED STATES PATENT AND TRADEMARK OFFICE
CERTIFICATE OF CORRECTION

PATENT NO.    : 6,017,735
DATED         : January 25, 2000
INVENTOR(S)   : Peter Francis Joseph O' Hare and Gillian Daphne Elliott It is certified that error appears in the above-identified patent and that said Letters Patent is hereby corrected as shown below:

Column 3,
Line 18, "94121807" should be -- 94/21807 --;

Column 4,
Line 36, "SHV" should be -- BHV --;
Line 43, "M14891." should be -- M14891, --;
Line 55, "95112673" should be -- 95/12673 --;

Column 5,
Line 3, "comprising. the" should be -- comprising the --;
Line 9, "entigenic" should be -- antigenic --;

Column 8,
Line 56, "73-325 6r 45-336" should be -- 75-325 or 75-336 --;
Line 63, "5,573.925" should be -- 5,573,925 --;

Column 10,
Line 8, "Paris, M." should be -- Paris: M. --;
Line 22, "(1997). a" should be -- (1997), a --;
Line 45, "antigens-" should be -- antigens --;

Column 11,
Line 6, "Boon. Adv." should be -- Boon, Adv --;
Line 47, "177-210. and" should be -- 177-210, and --;
Line 51, "(1992). pp 624-629" should be -- (1992) pp 624-629 --;

Column 12,
Line 57, "With" should be -- with --;

Column 13,
Line 54, "immunornodufating" should be -- immunomodulating --;
Line 60, "andlor" should be -- and/or --;
Line 67, "applications: thus for" should be -- applications: thus, for --;

Column 15,
Line 4, "dependent an" should be -- dependent on --;
Line 45, "pc4gepB" should be -- pc49epB --;
Line 63, "O'Hare. 1997)" should be -- O'Hare, 1997) --;

UNITED STATES PATENT AND TRADEMARK OFFICE
CERTIFICATE OF CORRECTION

PATENT NO.   : 6,017,735
DATED        : January 25, 2000
INVENTOR(S)  : Peter Francis Joseph O' Hare and Gillian Daphne Elliott It is certified that error appears in the above-identified patent and that said Letters Patent is hereby corrected as shown below:

Column 16,
Line 60, "Litwak, G. Gebhardt" should be -- Litwak, G., Gebhardt --;

Column 18,
Line 5, "6: 177-185." should be -- 8: 177-185. --;
Line 6, "p53. the" should be -- p53, the --.

Signed and Sealed this

Twenty-third Day of July, 2002

Attest:

JAMES E. ROGAN
*Attesting Officer*          *Director of the United States Patent and Trademark Office*